(12) United States Patent
Duong et al.

(10) Patent No.: US 9,101,343 B2
(45) Date of Patent: Aug. 11, 2015

(54) THERAPEUTIC CRYOABLATION SYSTEM

(76) Inventors: Thach Buu Duong, Tustin, CA (US);
Min Frank Zeng, Irvine, CA (US)

( * ) Notice: Subject to any disclaimer, the term of this patent is extended or adjusted under 35 U.S.C. 154(b) by 373 days.

(21) Appl. No.: 13/566,071

(22) Filed: Aug. 3, 2012

(65) Prior Publication Data

US 2014/0039476 A1 Feb. 6, 2014

(51) Int. Cl.
*A61B 18/02* (2006.01)
*A61B 18/00* (2006.01)

(52) U.S. Cl.
CPC ....... *A61B 18/02* (2013.01); *A61B 2018/00041* (2013.01); *A61B 2018/0212* (2013.01); *A61B 2018/0262* (2013.01)

(58) Field of Classification Search
USPC .......................................................... 606/21
See application file for complete search history.

(56) References Cited

U.S. PATENT DOCUMENTS

| | | | | |
|---|---|---|---|---|
| 5,674,218 | A * | 10/1997 | Rubinsky et al. | 606/20 |
| 6,468,268 | B1 * | 10/2002 | Abboud et al. | 606/20 |
| 2002/0037081 | A1 | 3/2002 | Rogoff et al. | |
| 2002/0111612 | A1 | 8/2002 | Lalonde et al. | |
| 2002/0156469 | A1 | 10/2002 | Yon et al. | |
| 2002/0177845 | A1 | 11/2002 | Heiner et al. | |
| 2003/0078570 | A1 | 4/2003 | Heiner et al. | |
| 2003/0125721 | A1 | 7/2003 | Yon et al. | |
| 2003/0220634 | A1 | 11/2003 | Ryba et al. | |
| 2004/0024413 | A1 | 2/2004 | Lentz et al. | |
| 2004/0034344 | A1 | 2/2004 | Ryba | |
| 2004/0034345 | A1 | 2/2004 | Lentz | |
| 2004/0116916 | A1 | 6/2004 | Lentz | |
| 2004/0116917 | A1 | 6/2004 | Lentz | |
| 2004/0116965 | A1 | 6/2004 | Falkinberg | |
| 2004/0158238 | A1 | 8/2004 | Lalonde et al. | |
| 2004/0267250 | A1 | 12/2004 | Yon et al. | |
| 2005/0159735 | A1 | 7/2005 | Walton et al. | |
| 2005/0177053 | A1 | 8/2005 | Boveja et al. | |
| 2005/0198972 | A1 | 9/2005 | Lentz et al. | |
| 2005/0228368 | A1 | 10/2005 | Yon et al. | |
| 2005/0240239 | A1 | 10/2005 | Boveja et al. | |
| 2005/0288657 | A1 | 12/2005 | Lentz et al. | |
| 2006/0004349 | A1 | 1/2006 | Ryba et al. | |
| 2006/0004350 | A1 | 1/2006 | Ryba | |
| 2006/0004351 | A1 | 1/2006 | Arless et al. | |
| 2007/0016274 | A1 | 1/2007 | Boveja et al. | |
| 2007/0031338 | A1 | 2/2007 | Zabinski | |
| 2007/0276360 | A1 | 11/2007 | Johnston et al. | |
| 2007/0277550 | A1 | 12/2007 | Li et al. | |
| 2007/0299432 | A1 | 12/2007 | Arless et al. | |
| 2008/0065179 | A1 | 3/2008 | Yon et al. | |
| 2008/0077124 | A1 | 3/2008 | Lalonde | |
| 2008/0114345 | A1 | 5/2008 | Arless et al. | |
| 2009/0125008 | A1 * | 5/2009 | Levin | 606/21 |
| 2009/0234345 | A1 | 9/2009 | Hon | |

(Continued)

*Primary Examiner* — Carl H Layno
*Assistant Examiner* — Jennifer Ghand
(74) *Attorney, Agent, or Firm* — Raymond Sun

(57) ABSTRACT

A cryoablation system has a gas source which provides a working gas at room temperature and at a constant set pressure. The system also includes a liquid generator which is coupled to the gas source to receive the working gas, and which then generates a working cryogen fluid in a liquid phase that operates at a temperature and pressure that lies on its Joule-Thomson Inversion Curve, with the Joule-Thomson coefficient maintained within the range 0.00±0.08 degrees F./Atmosphere. The system also includes a catheter coupled to the liquid generator for receiving the working cryogen, the catheter having a distal section which delivers the working cryogen to a treatment location.

8 Claims, 19 Drawing Sheets

(56) References Cited

U.S. PATENT DOCUMENTS

| | | |
|---|---|---|
| 2009/0318913 A1 | 12/2009 | Li |
| 2010/0179526 A1 | 7/2010 | Lawrence |
| 2010/0249765 A1 | 9/2010 | Johnston |
| 2010/0256621 A1 | 10/2010 | Babkin et al. |
| 2010/0280507 A1 | 11/2010 | Babkin et al. |
| 2011/0009854 A1 | 1/2011 | Babkin et al. |
| 2011/0028960 A1 | 2/2011 | Tin |
| 2011/0040297 A1 | 2/2011 | Babkin et al. |
| 2011/0054452 A1 | 3/2011 | Chun |
| 2011/0087206 A1* | 4/2011 | Geiselhart et al. ............ 606/23 |
| 2011/0196359 A1 | 8/2011 | Arless et al. |
| 2012/0016355 A1 | 1/2012 | George et al. |
| 2012/0053575 A1 | 3/2012 | Babkin et al. |
| 2012/0059364 A1* | 3/2012 | Baust et al. .................... 606/24 |
| 2012/0065554 A1 | 3/2012 | Pikus |
| 2012/0065631 A1 | 3/2012 | Arless et al. |

* cited by examiner

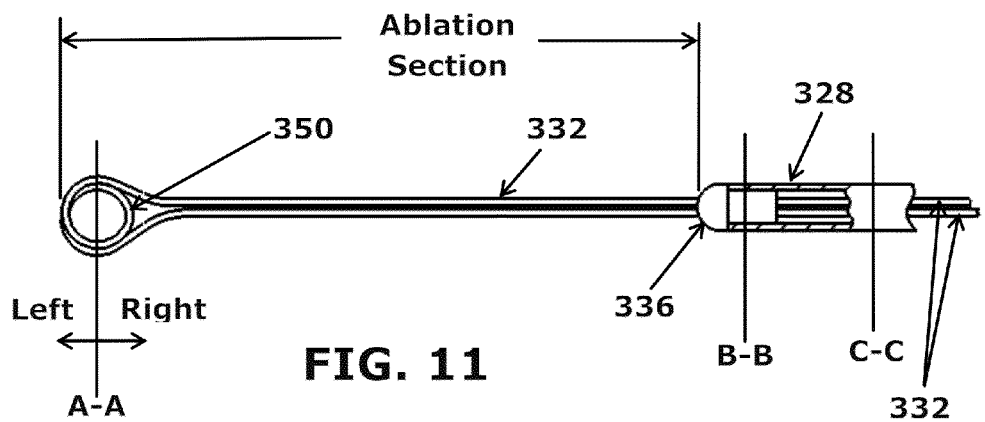
FIG. 11
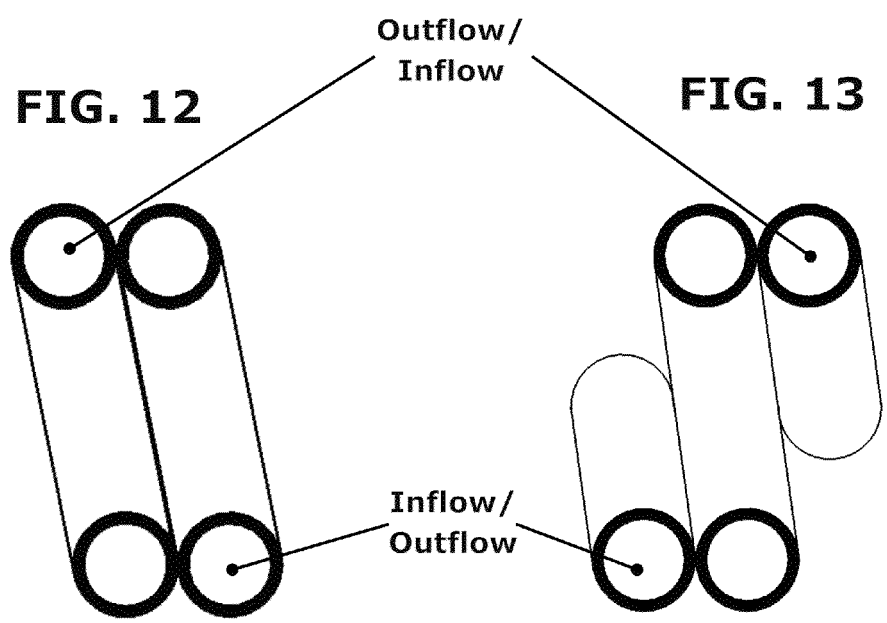
FIG. 12
FIG. 13

FIG. 18
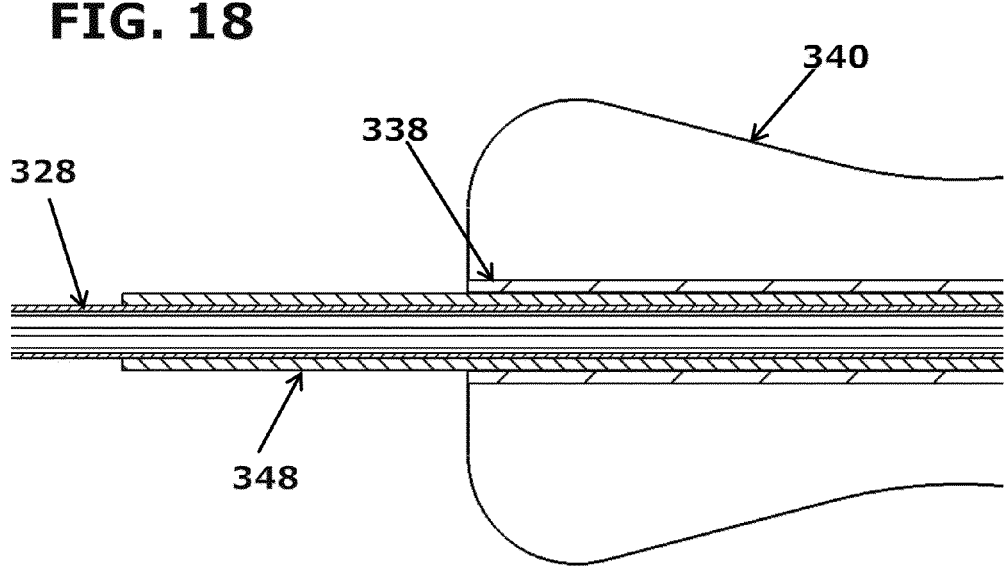
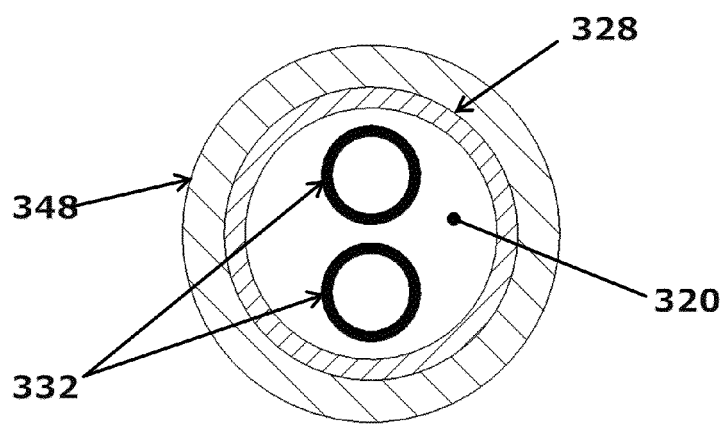
FIG. 19

Detail View K

THERAPEUTIC CRYOABLATION SYSTEM

BACKGROUND OF THE INVENTION

1. Field of the Invention

The present invention relates to a medical device, and in particular, a cryoablation catheter and system for freezing and destroying biological tissues.

2. Description of the Prior Art

Cryosurgical therapy involves the application of extremely low temperature and complex systems designed to suitably freeze the target biological tissue to be treated. Many of these systems use cryoprobes with particular shapes and sizes that are designed to contact a selected portion of the tissue without undesirably effecting adjacent healthy tissues or organs. Extreme freezing is produced with refrigerants that are introduced through a flexible or rigid probe. The freezing is then applied to the target tissue through a heat transfer element formed as a part of the probe and limited to applying the freezing to a relatively small location.

SUMMARY OF THE DISCLOSURE

It is an object of the present invention to provide an improved cryoablation catheter and system for freezing and destroying biological tissues.

In order to accomplish the objects of the present invention, the present invention provides a cryoablation system having a gas source which provides a working gas at room temperature and at a constant set pressure. The system also includes a liquid generator which is coupled to the gas source to receive the working gas, and which then generates a working cryogen fluid in a liquid phase that operates at a temperature and pressure that lies on its Joule-Thomson Inversion Curve, with the Joule-Thomson coefficient ($\mu$) maintained within the range 0.00±0.08 degrees F./Atmosphere. The system also includes a catheter coupled to the liquid generator for receiving the working cryogen, the catheter having a distal section which delivers the working cryogen to a treatment location.

According to one embodiment of the present invention, the working gas is used for both warming and cooling purposes.

According to another embodiment of the present invention, the distal section is bendable around a contour having an angle of less than ninety degrees with a bend radius being less than 0.50 inch, and the catheter includes at least one tube having a lumen that circulates the working cryogen from its proximal end to its distal section and then back to the proximal end.

BRIEF DESCRIPTION OF THE DRAWINGS

FIG. 11 is a side view of the distal section of one embodiment of the catheter of FIG. 10.

FIGS. 12 and 13 are left and right cross-sectional views, respectively, taken along line A-A in FIG. 11.

FIG. 18 is an enlarged view of the area E in FIG. 16.

FIG. 19 is a cross-sectional view taken along line F-F in FIG. 16.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The Ablation System

Figure 1:
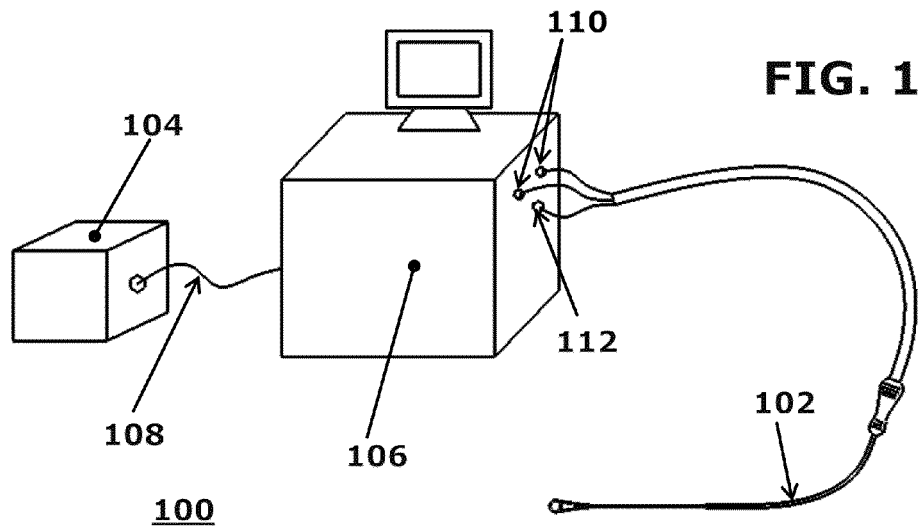
FIG. 1 illustrates a cryoablation system according to the present invention.

Referring to FIG. 1, the present invention provides a cryoablation system 100 that delivers both cold and warm energy to the distal end of a catheter 102 using low-pressure gas, such as nitrogen, helium, argon, neon, etc. The system 100 has a gas source module 104 that supplies working gas to an ablation system 106 through a flexible hose assembly 108. The ablation system 106 receives, directs, transforms, and controls the flow working fluid within the system 100. The ablation system 106 incorporates electrical on/off solenoid valves used to direct gas flow to and from the catheter 102 using computer-controlled software. The ablation system 106 contains a vacuum insulated storage tank/Dewar to store liquid refrigerant which is used to sub-cool the working fluid. The sub-cooled fluid then exits the ablation system 106 through one of two female gas connectors 110. The catheter 102 has two mating interchangeable male gas connectors, where one connector 110 connects and receives the sub-cooled/heated fluid from the ablation system 106. A delivery line positioned within the catheter 102 connects to the female gas connector 110 carrying the working fluid to the distal end of the catheter 102. The working fluid is then circulated back through a loop/manifold into a second delivery line which is positioned parallel to the first delivery line of the catheter 102. The second delivery line connects to the second gas connector 110 at the connector end, and delivers the used fluid from the catheter 102 back into the ablation system 106.

The ablation system also incorporates an active ultra-high vacuum system for thermal insulation purposes. The vacuum system communicates with the catheter vacuum chamber 320 (as described in connection with FIGS. 15, 17, 19, 20, 21 and 24 hereinbelow) via a mechanical vacuum connector 112 and provides a vacuum level to maintain proper thermal insulation to the cryogenic delivery lines against atmospheric heat.

The system 100 of FIG. 1 has built-in mechanical and software safety features to monitor, detect, and control abnormal system responses, as explained in greater detail below.

Figure 2:
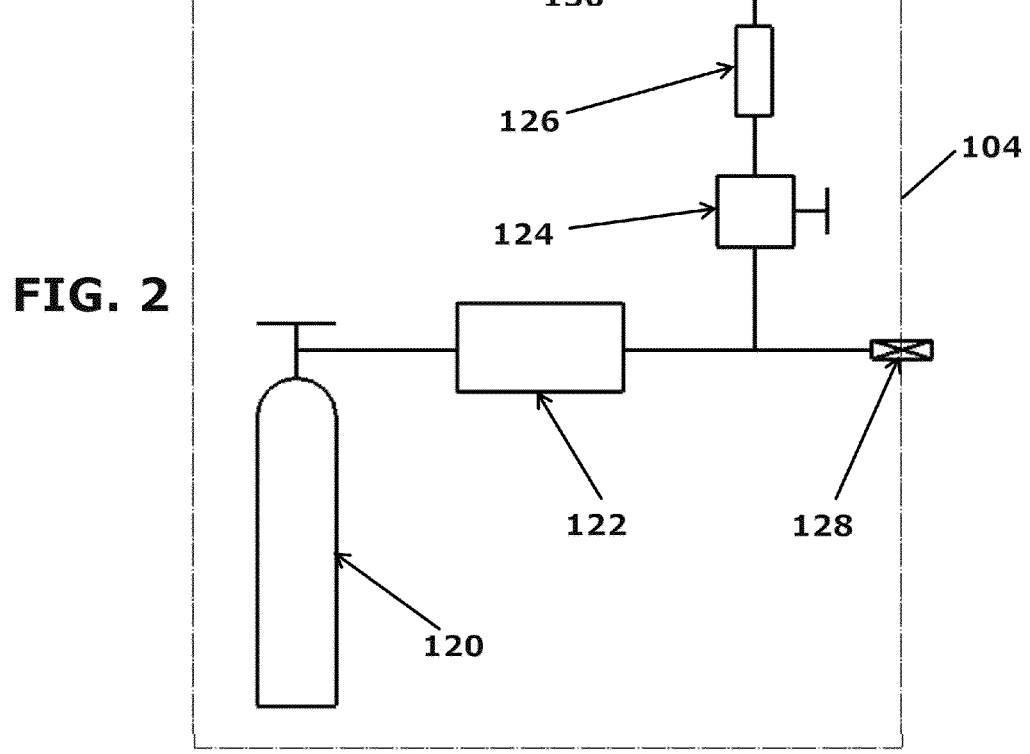
FIG. 2 is a schematic diagram of the gas source module of the system of FIG. 1.

Referring to FIG. 2, the gas source module 104 includes a tank 120 that contains highly compressed nitrogen gas up to approximately 400 atmospheres, a regulator 122 coupled to the tank 120, a manual on/off bleed valve 124, a muffler/silencer 126, and a gas source connector 128. An inline pressure regulator reduces high-pressure gas within a pressure range of approximately 20 atmospheres to 100 atmospheres. An exhaust 130 relieves gas trapped within the pressure line. The gas source connector 128 connects to the outlet of the regulator 122 on one end, and interfaces with the flexible hose assembly 108 at the other end.

Figure 3:
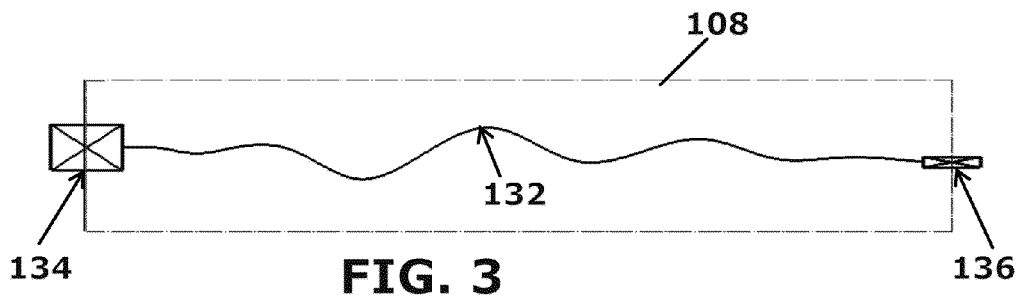
FIG. 3 illustrates the flexible hose assembly of the system of FIG. 1.

The outlet gas from the gas source module 104 is provided to the ablation system 106 through the flexible hose assembly 108. Referring to FIG. 3, the flexible hose assembly 108 has a hose 132 that has a first end that has a female gas connector 134 that has an integrated spring loaded valve. The spring loaded valve opens when mated to a male connector 128 of the gas source module 102. At the second end of the hose 132 is a male gas connector 136 that is connected to the female gas connector 138 at the ablation system 106 (see FIG. 4). Having a male-female connection arrangement prevents gas entrapment between the connector ends if a disconnection occurred while the line is still pressurized.

Regulated gas from the flexible hose assembly 108 will first enter the gas inlet module 140. The outlet of the inlet gas module 140 then splits into two paths to a freeze module 142 and a thaw module 144. The outlets of the freeze module 142 and the thaw module 144 are joined at Point E that leads to one of two female gas connectors 110. The mating male connector of the catheter 102 is connected to this gas connector 110 and receives cryogenic/warm fluid. The other gas connector 110 is connected to a secondary mating connector from the catheter 102, and delivers the used fluid back into the ablation system 106 to pre-cool the inlet gas from the gas source module 104. The system 100 also has a female vacuum connector 112 that communicates with the male vacuum connector at the catheter 102. The two gas connectors 110 are interchangeable, but the vacuum connector 112 is not interchangeable with the gas connectors 110.

Figure 5:
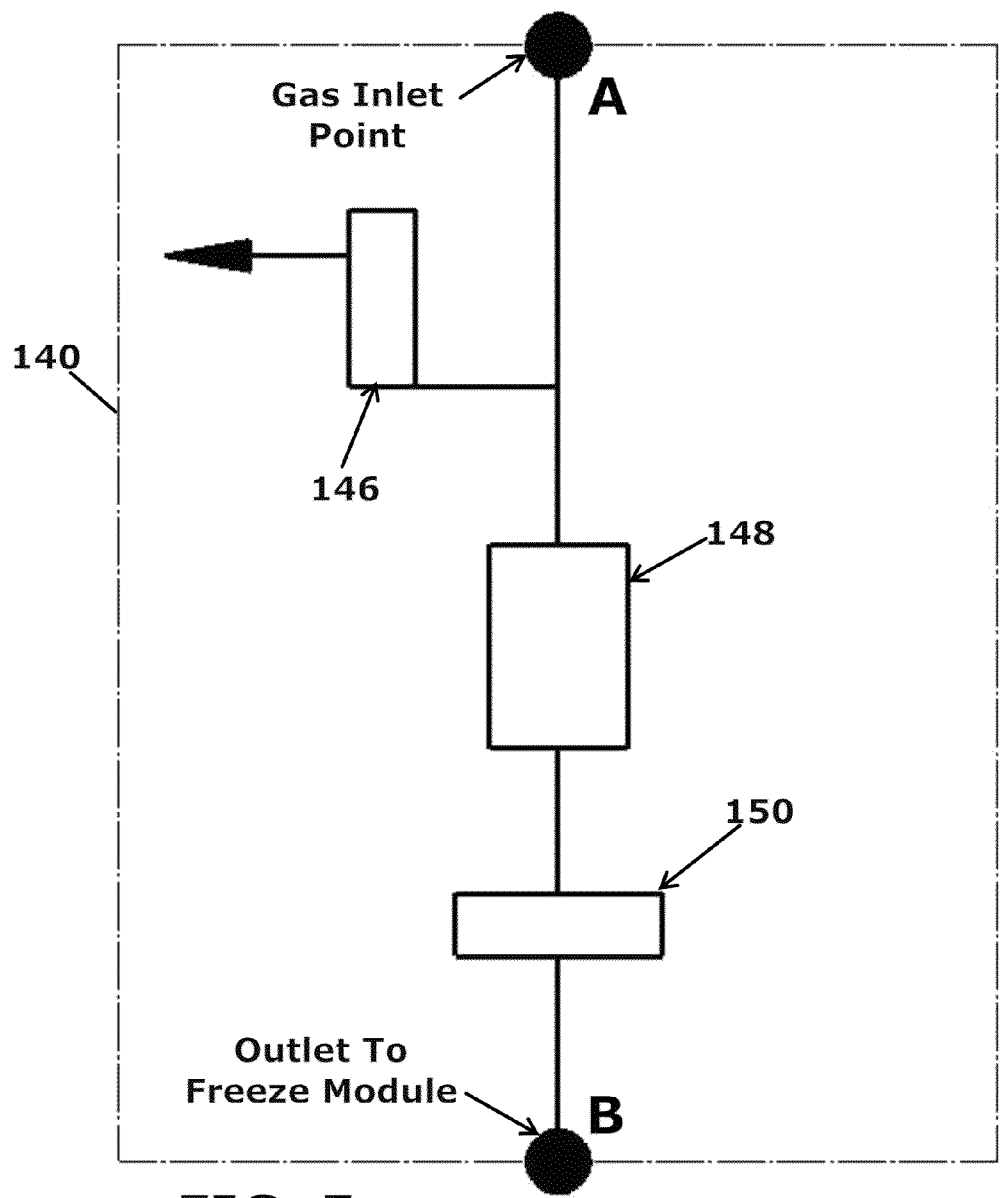
FIG. 5 is a schematic diagram of the gas inlet module of the ablation system of FIG. 4.

Referring to FIG. 5, the function of the gas inlet module 140 is to limit the maximum operating gas pressure, and to control the quality of the working gas. The gas inlet module 140 contains a pressure relief valve 146, a moisture filter 148, and a particle filter 150. The pressure relief valve 146 automatically purges excessive pressure above the set point to prevent over-pressurization. Over-pressurization is usually due to user error in setting the improper regulator pressure at the gas source module 104. The moisture filter 148 and the particle filter 150 trap contaminants that otherwise would migrate and clog the flow passage area. Moisture solidifies as its temperature reduces to zero degrees Celsius, and can therefore block the flow area. Particles can collect and accumulate at small passages, and thereby clog up the flow passage.

Figure 6:
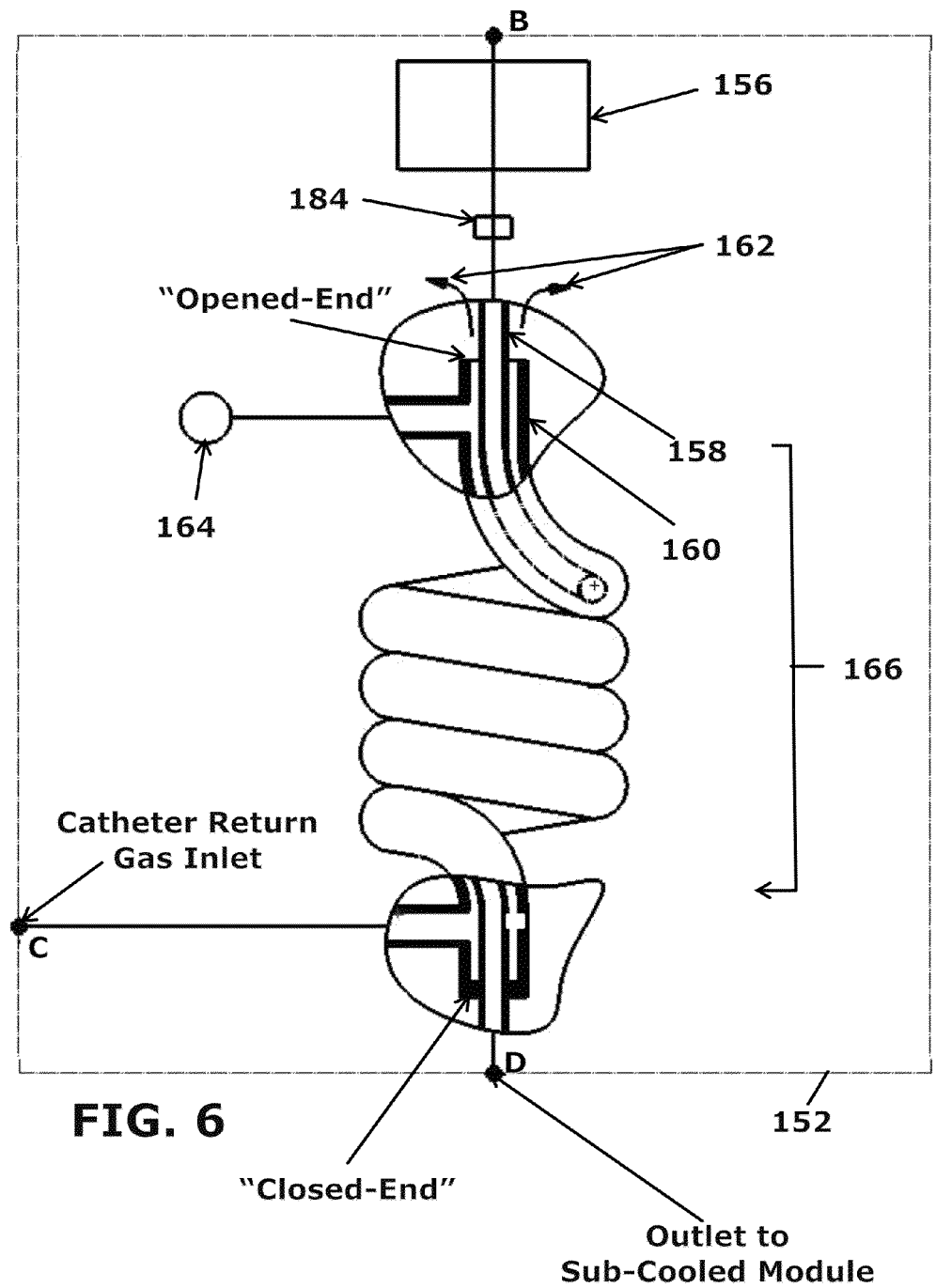
FIG. 6 is a schematic diagram of the first stage pre-cooled module of the ablation system of FIG. 4.
Figure 7:
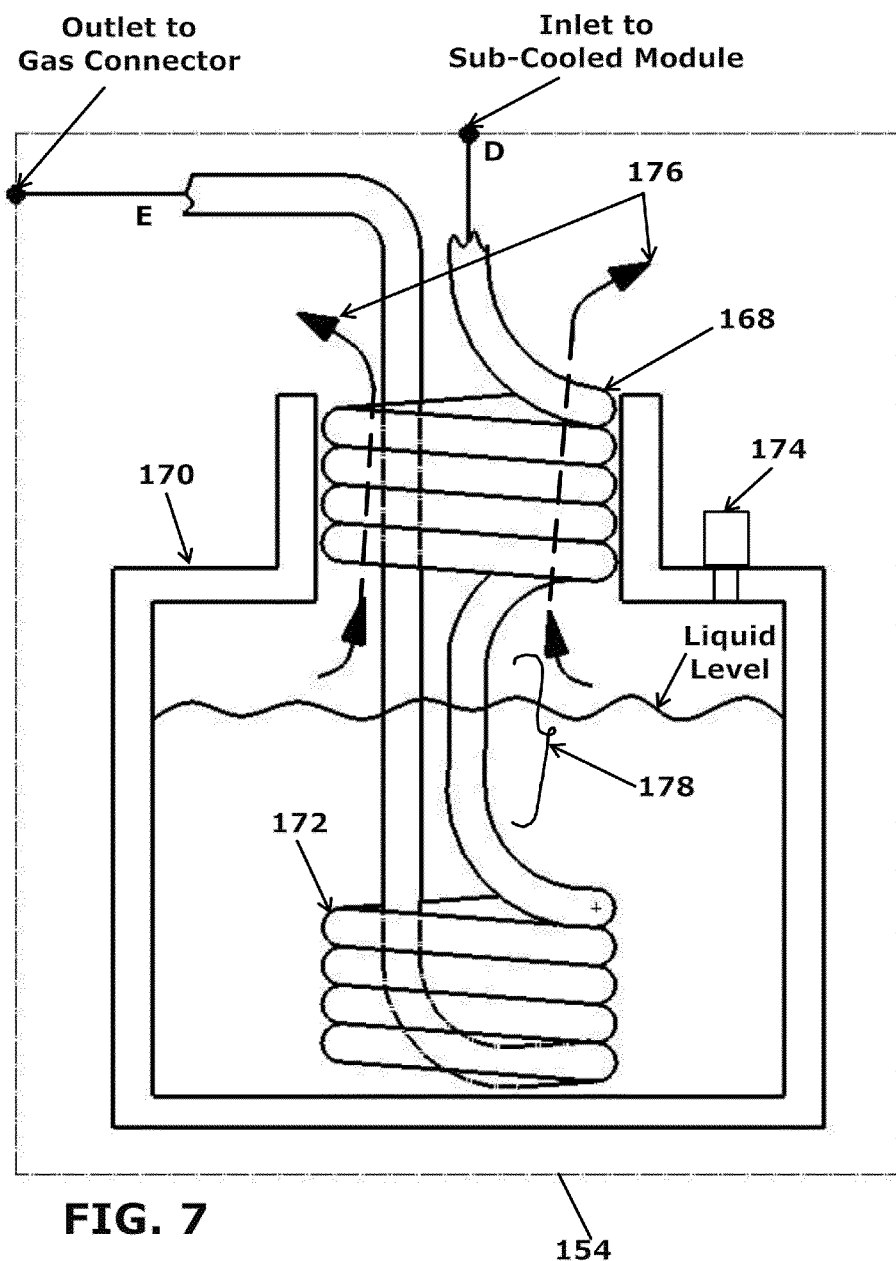
FIG. 7 is a schematic diagram of the sub-cooled module of the ablation system of FIG. 4.

The freeze module 142 contains two sub-modules, a first stage pre-cooled module 152 (see FIG. 6, hereinafter "FSPM")), and a sub-cooled module 154 (see FIG. 7). During the freeze cycle, outlet gas from the inlet gas module 140 feeds into the FSPM 152. Activating a normally closed "Freeze" solenoid valve 156 allows gas to flow into a "tube-in-tube" first-stage heat exchanger 166 that is constructed with two concentric tubes: an inner tube 158 and an outer tube 160. The inner tube 158 carries the working fluid. The space between the inner tube 158 and outer tube 160 carries the return gas 162 from the catheter 102. The gap between the outer tube 160 and inner tube 158 is filled with brazing material forming a pressure tight seal at one end. The gap at the other end of the heat exchanger 166 is opened. The return gas from the catheter 102 enters the heat exchanger 166 starting from Point C in FIGS. 4 and 6, near the closed end of the heat exchanger 166. The return gas 162 then travels counter-flow to the direction of the inlet gas, and exhausts to the atmosphere at the opened end of the heat exchanger 166. The FSPM 152 has an integrated pressure transducer 164 that is positioned near the opened end of the heat exchanger 166. Its function is to monitor the return gas pressure. Information collected from the transducer 164 is used to evaluate system performance and for diagnostic purpose.

With the outlets of the freeze module 142 and thaw module 144 connected to a common gas connector 110, gas can backflow from one module into another module. A check valve 184 (see FIGS. 6 and 8) is incorporated within each module 142 and 144 to prevent this condition. During a freeze or thaw cycle, the respective check valve 184 prevents gas flowing back into the inlet line.

Referring to FIG. 7, pre-cooled gas exiting the FSPM 152 immediately enters a second-stage pre-cooled heat exchanger 168 in the sub-cooled module 154. The second-stage heat exchanger is formed from a single coiled tube. The coil of the heat exchanger 168 is positioned at the neck of a Dewar 170, where vaporized gas converges. The evaporated gas 176 further cools the working fluid as the gas exits the Dewar 170. The working fluid (gas) then exits the coiled section of the second-stage pre-cooled heat exchanger 168 into a straight tube section 178 that is fluidly coupled to the inlet of the sub-cooled heat exchanger 172, which is also formed from a single coiled tube. The sub-cooled heat exchanger 172 is positioned at the bottom of the Dewar 170 where it is submerged within the refrigerant fluid. The working fluid undergoes a phase change to liquid cryogen as it exits the sub-cooled heat exchanger 172. The cryogen is then transported to a female gas connector 110 delivering cryogenic fluid to the catheter 102.

The Dewar 170 is an open storage tank. Evaporated gas is allowed to easily escape before accumulating and building up Dewar pressure. As a secondary safety feature, the Dewar 170 is designed with an integral pressure relief valve 174 to relieve excessive pressure and prevent over-pressurization.

Figure 8:
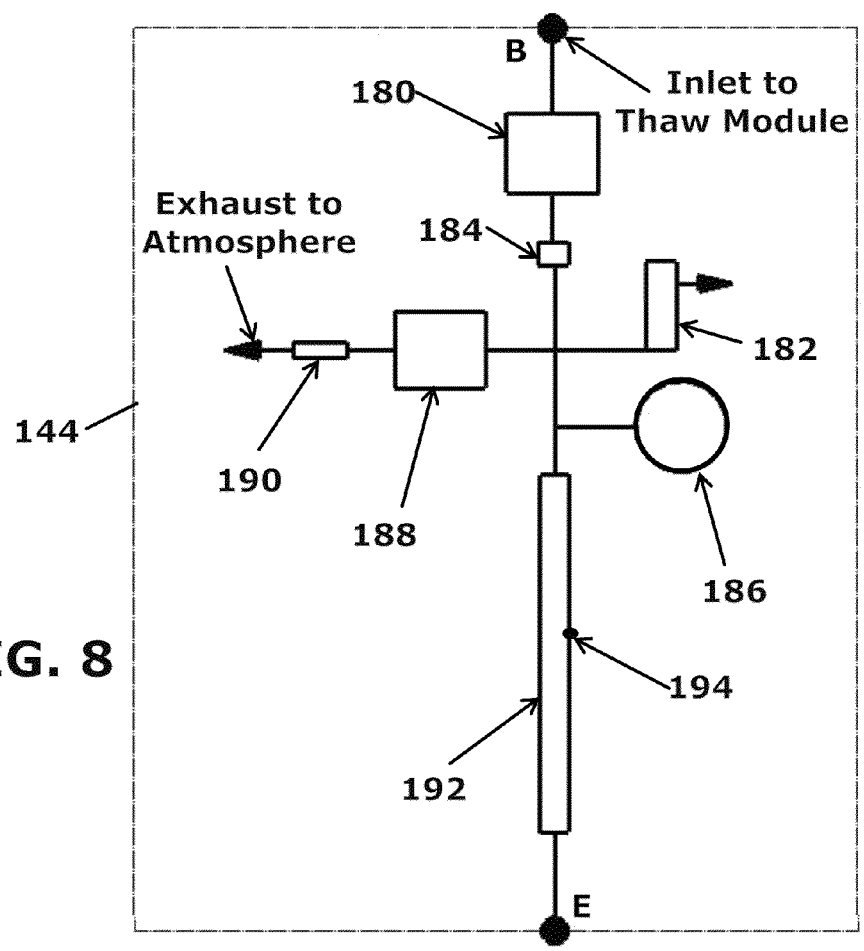
FIG. 8 is a schematic diagram of the thaw module of the ablation system of FIG. 4.

The outlet from inlet gas module 140 can also feed into the thaw module 144 (see FIG. 8). Thawing is desirable at the beginning of a procedure and after a freeze cycle. At the beginning of the procedure, thawing removes residual moisture collected, and flushes the system 100 of contaminants. Residual moisture will clog up the flow passage as it turns to ice, or it can significantly narrow the flow passage, thereby preventing the proper amounts of cryogen from being delivered by the catheter 102 to the ablation region. At the end of the freeze cycle, with the catheter embedded/stuck inside the volume of ice formed during freezing, thawing is required to melt the ice around the catheter 102, allowing the removal or repositioning of the catheter 102. The thawing cycle is started by activating a normally-closed "Thaw" solenoid valve 180, allowing delivery of warm gas into the gas connector 110. System software prevents simultaneous activation of both the "Freeze" valve 156 and the "Thaw" valve 180, as this would cause system inefficiency. The thaw module 144 incorporates a check valve 184, as in the freeze module 142, for the same purpose. A pressure relief valve 182 prevents system overpressurization, especially when the catheter 102 is connected. In the case of a clogged catheter 102, trapped fluid accumulates heat and causes a rise in pressure as its volume grows. The pressure relief valve 182 automatically purges excessive pressure from the system. As a secondary safety feature, a pressure transducer 186 installed within the delivery line monitors the fluid pressure digitally. This information feeds into the system software. At the detection of an abnormal pressure level, the software will trigger a purge cycle. The purge cycle involves activating a "Purge" solenoid valve 188, and deactivating both the "Freeze" and "Thaw" solenoid valves 156 and 180. Deactivating the "Freeze" and "Thaw" solenoid valves 156 and 180 will stop the gas supply. Activating the "Purge" solenoid valve 188 evacuates all trapped gas in between the fluid lines connecting the "Freeze" to the "Thaw" solenoid valves 156 and 180, with the trapped gas being evacuated to the atmosphere via a silencer 190. Both the pressure relief valve 182 and pressure transducer 186 sense the inlet fluid pressure to the catheter 102 during both freeze and thaw cycles.

Figure 4:
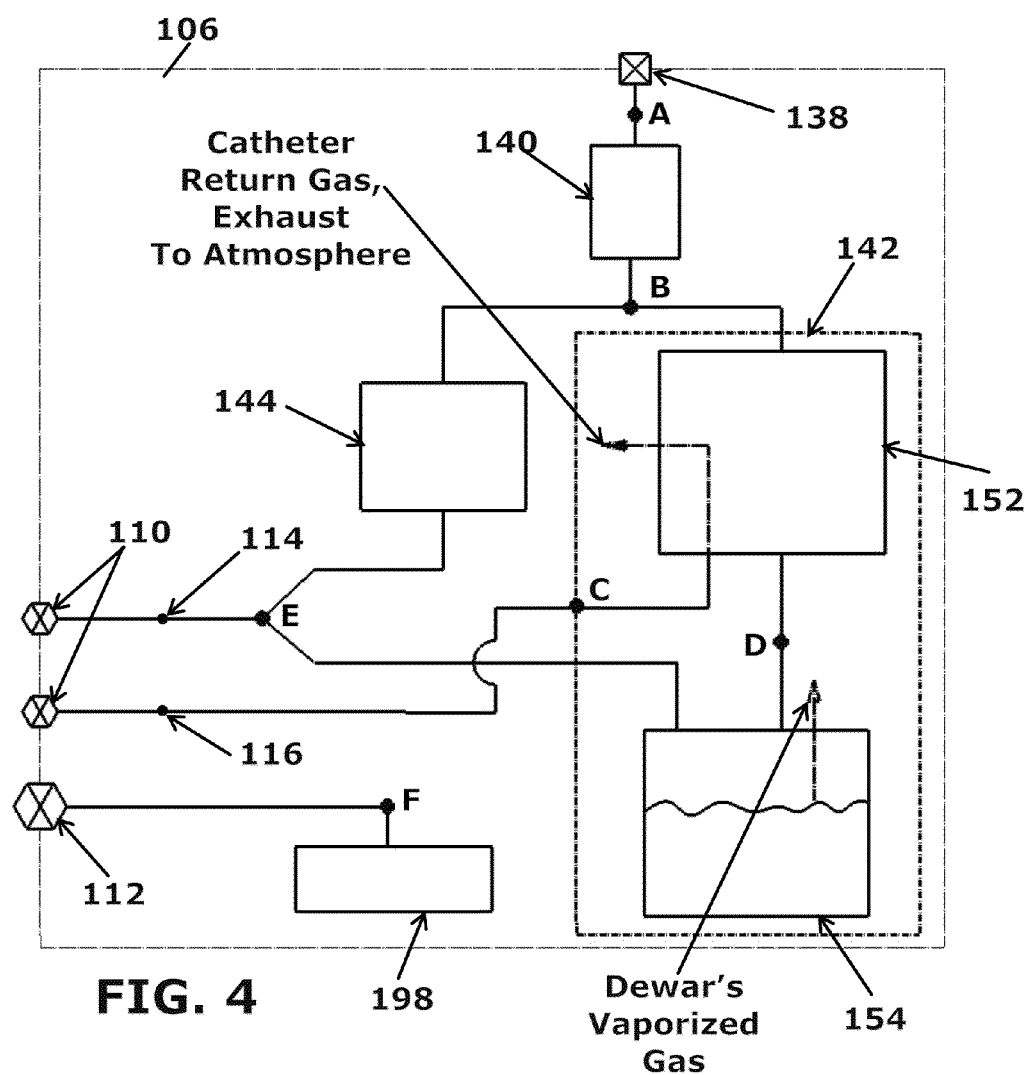
FIG. 4 is a schematic diagram of the ablation system of the system of FIG. 1.

In normal operation, working fluid (gas) enters the thaw module 144 at Point B (see FIGS. 4 and 8), passes through the thaw valve 180 and the check valve 184, and then through an optional in-line heater 192, and then to the gas connector 110 via Point E. Referring to FIG. 4, temperature sensors 114 and 116 are coupled to the gas connectors 110 to sense the temperature of the working fluid (gas).

Figure 9:
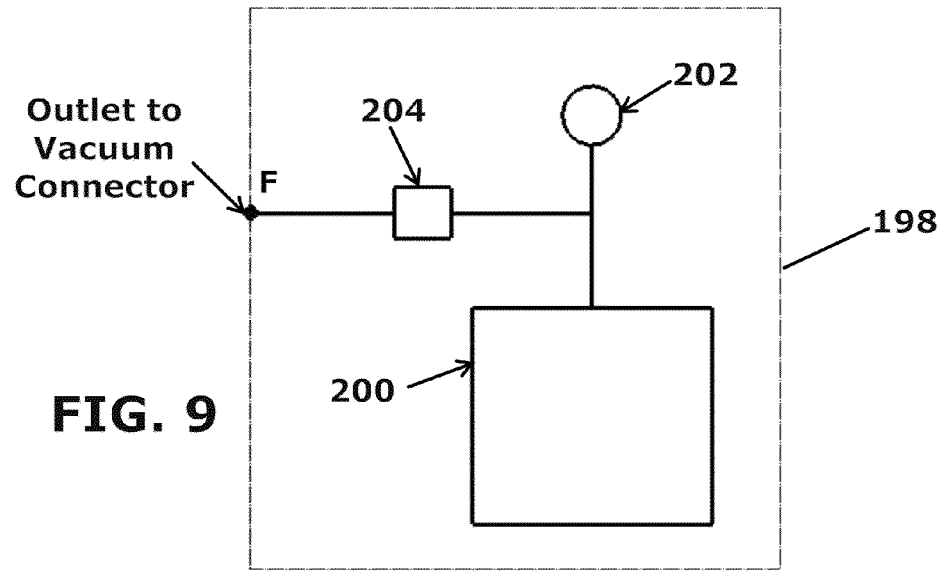
FIG. 9 is a schematic diagram of the vacuum module of the ablation system of FIG. 4.
Figure 10:
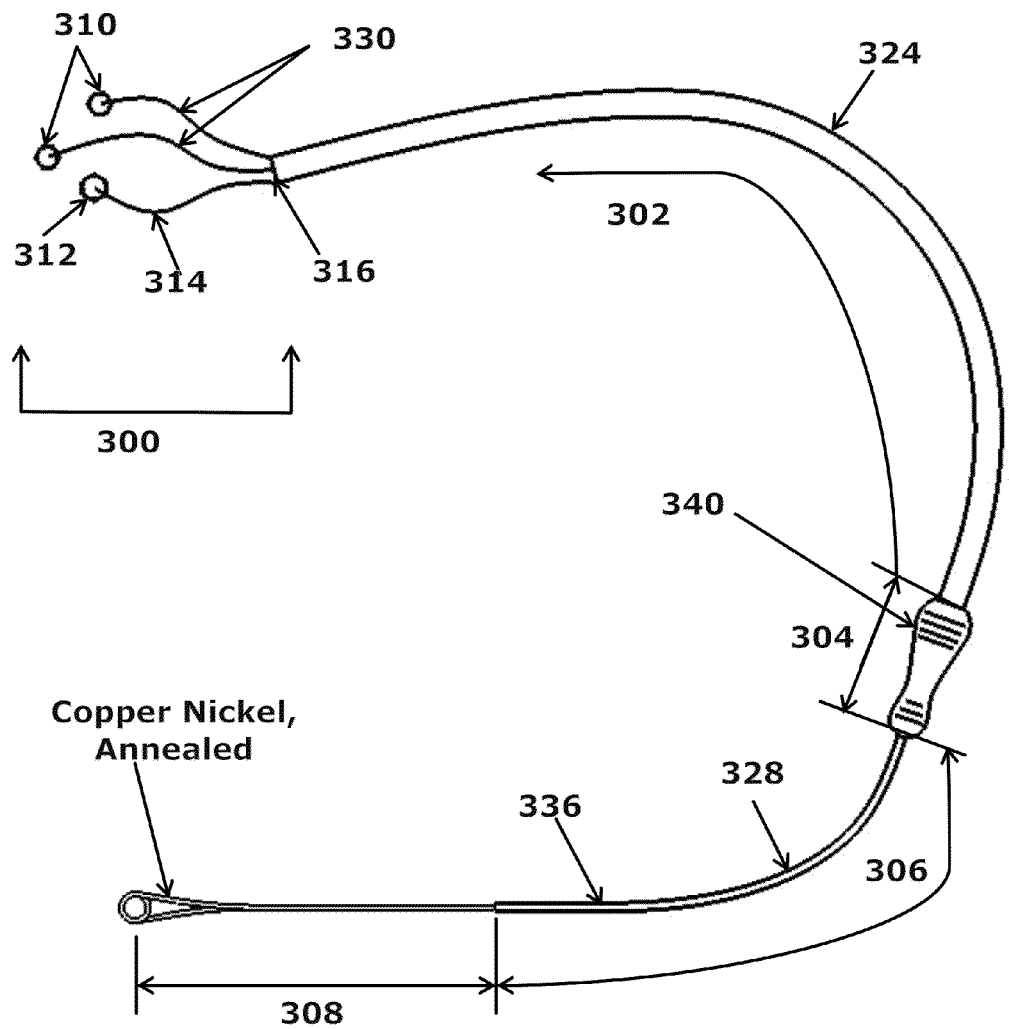
FIG. 10 illustrates the catheter of the system of FIG. 1.
Figure 14:
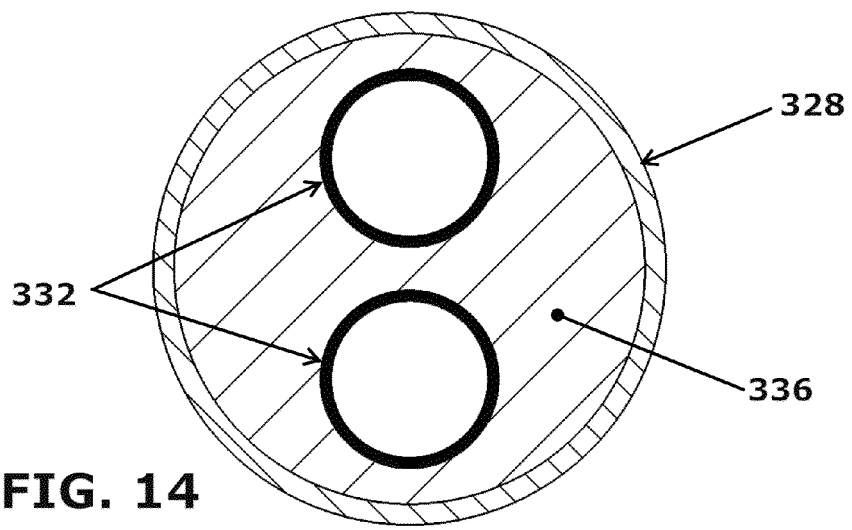
FIG. 14 is a cross-sectional view taken along line B-B in FIG. 11.
Figure 15:
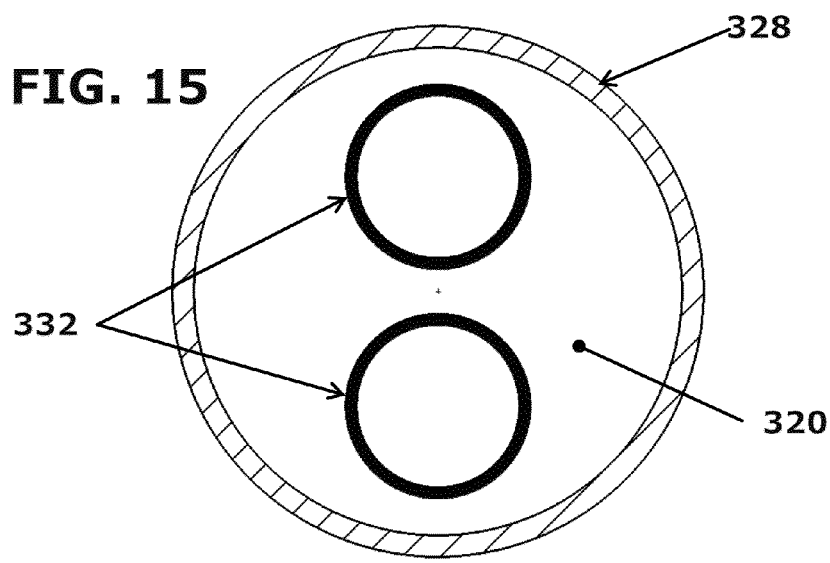
FIG. 15 is a cross-sectional view taken along line C-C in FIG. 11.

Referring to FIGS. 4 and 9, a vacuum module 198 is also incorporated within the ablation system 106 to provide thermal vacuum insulation to protect the cryogenic fluid from evaporation due to ambient heat. In a perfect vacuum environment, no particles are present to conduct heat from a hot surface to the cold surface. Molecular motion is not available to carry heat from a hot surface to a cold surface either. Therefore, two major modes of heat transfer (i.e., heat conduction and convection) are eliminated. Eliminating the third mode, radiation heat transfer, requires additional shielding. In the present invention, the heat gain from conduction is the most dominant and it is desired to eliminate it.

In practice, it is difficult and impractical to provide a perfect vacuum environment. Fortunately, a perfect vacuum environment is not needed for the present invention. The present invention has two primary objectives. First, it seeks to provide a sufficient level of insulated protection against ambient heat to maintain a certain level of operating efficiency. The present invention attempts to minimize the amount of time taken to deliver cold energy to the distal section 308 of the catheter 102 after activating a freeze cycle. If the catheter 102 not well insulated, the heat gain from the environment along the length of the catheter 102 will result in warm gas being delivered to the distal section 308 of the catheter 102. Second, the present invention seeks to protect the catheter 102 from freezing along the catheter body 306. While the present invention seeks to deliver and focus the cold energy at the distal section of the catheter 102, having cold energy spread along the catheter body 306 not only damages other body tissue, but also reduces the cooling power where needed.

To minimize heat gain by conduction requires a high vacuum level. The vacuum pressure has to be beyond a pressure level where gas conduction becomes dependent on its pressure. In an air-filled environment, the transition pressure from a pressure-dependent to a pressure independent is approximately 10-100 µm Hg. Beyond this pressure point, the thermal conductivity of the gas reduces abruptly. Further reduction in pressure reduces the thermal conductivity of the gas. From experiment in an air-filled environment at standard ambient temperature, it was determined that a vacuum level of 1 µm Hg higher is sufficient for the present invention.

The ablation system 100 employs an active vacuum system in its vacuum module 198, which has a vacuum pump unit 200, a vacuum pressure transducer 202, and a vacuum valve 204. The vacuum pump unit 200 has a two-stage vacuum pump. The first stage is a rough pump that can deliver a vacuum pressure of 10 Torr (1 Torr=1 mm Hg). The second stage, which can be a turbo molecular pump, can deliver a vacuum level of $10^{-8}$ Torr. Both of these pumps works together as a single pump unit. The outlet of the vacuum pump unit 200 splits out to the vacuum pressure transducer 202 and the vacuum valve 204. The vacuum valve 204 can be a normally closed, electrically controlled, on/off solenoid valve. The vacuum valve 204 isolates the vacuum pump unit 200 from the external environment. The pressure transducer 202 senses the vacuum pressure at the inlet of the second-stage vacuum pump, and its digital data is used to synchronize the operations of the two vacuum pumps. The pressure transducer 202 also functions to monitor and detect abnormal pressure level within the catheter vacuum chamber 320 (see FIGS. 15, 17, 19, 20, 21, and 24). Once the vacuum connector 112 is connected to the ablation system 100 and the vacuum valve 204 is activated, the vacuum module 198 and the catheter vacuum chamber 320 will be in communication. Any pressure spike within the catheter vacuum chamber 320 due to leakage from the gas line will be captured by the outer lumen of the catheter 102 and detected by the pressure transducer 202. A shutdown procedure will be triggered by the system software to purge the unwanted gas. The shutdown procedure involves deactivating both the "Freeze" and "Thaw" valves 156 and 180 (as described above), and activating the "purge" and vacuum valves 188 and 204. The vacuum pumps and the vacuum valve 204 remain on or opened unless the vacuum pressure spikes up to a set pressure of 1 mmHG. Once the set pressure is reached, the vacuum valve 204 closes and isolates the vacuum pump unit 200 from the high-pressure source. Exposure of the vacuum system beyond this limit will cause damage. The "purge" valve 188 stays on until the pressure reduces to near atmospheric pressure. At this point, it is safe to remove the catheter 102 and to inspect the catheter 102 and the system 100 for damage.

The vacuum pumps within the vacuum pump unit 200 can operate independently of the catheter 102. Once the catheter 102 is connected to the ablation system 100, activating the vacuum valve 204 will provide communication between the vacuum pump unit 200 and the catheter vacuum chamber 320. Thereafter, the pressure transducer 202 reads the system vacuum pressure. Once the pressure level reaches $10^{-3}$ Torr or 1 μm Hg, the system software then allows the user to perform the freeze cycles.

Overall, the present invention features an open-system where the system 100 receives an external gas source, internally controls and directs the gas source, feeds the gas to a catheter, garnishes the cold energy from the return gas of the catheter, and then exhausts it to the atmosphere. Not reusing or recirculating the used gas makes this system an open-system. The system receives high-pressured gas (e.g., 10 atmospheres to 150 atmospheres) at room temperature. The system refrigerant sub-cools the incoming working fluid (gas). The refrigerant supplied by re-fillable liquid cryogens is stored in a Dewar 170 within the system 100. External gas is converted into liquid cryogen as it passes through a submerged heat exchanger 172 positioned at the bottom of the Dewar 170. Thawing power is supplied by room temperature gas, and or by using an in-line heater 192. The system 100 has built-in safety mechanisms, such as mechanical relief valves 146, 174 and 182, electrical relief valve 188, particle filter 150, and moisture filter 148. Electrically controlled on/off solenoid valves 156, 180, 188 and 204 are utilized to direct the gas flow. Check valves 184 are incorporated into the system 100 to prevent backflow. A mechanical pressure relief valve 174 is also built into the Dewar 170 to prevent over-pressurization due to vaporization of liquid cryogen. The in-line heater 192 works with a temperature sensor 194 to provide feedback for monitoring and controlling. Temperature and pressure sensors 114, 116 and 164 and 186 are incorporated to monitor both system and catheter performances.

Thus, the system 100 of the present invention provides several important benefits:

i. An external gas source (i.e., module 104) supplies the system 100 its working medium at room temperature and at a constant set pressure within the range of 10 atm to 150 atm.

ii. Inlet gas is sub-cooled by cryogenic fluid stored within the system 100 (i.e., a Dewar tank 170).

iii. The cold return gas from the catheter 102 is used to pre-cool incoming gas.

iv. The system 100 contains an active vacuum pump 198 to provide thermo/vacuum insulation.

vi. The vacuum pump 198 performs a safety function by evacuating any unwanted gas leakage from the catheter 102 that would otherwise migrate into the patient.

vii. The system has an automated leakage monitoring and detection system (i.e., thaw module 144) that has an automated software purge and shutdown procedure to protect the patient.

viii. The system 100 is configured so that thawing of the catheter 102 can be achieved by using room temperature gas, or combined with an in-line heater 192.

The Catheter

Referring to FIG. 10-24, the catheter 102 has a connector section 300, a hose section 302, a proximal section 304, a catheter body 306, and a distal section 308 that functions as an ablation section.

Referring to FIGS. 10 and 22-24, the connector section 300 has two interchangeable gas connectors 310 and a vacuum connector 312. The gas connectors 310 are connected to corresponding gas connectors 110 in the ablation system 100 to receive cold/warm fluid, and to circulate liquid cryogen from the connector end of the catheter 100 to the distal section 308, and then back to the connector end. The vacuum connector 312 is connected to a short vacuum tube 314, which terminates at an air-tight seal 316 located near the hose section 302. The vacuum tube 314 can be made of brass alloy or copper material. The internal opening of the vacuum tube 314 communicates with the catheter vacuum chamber 320 (see FIGS. 11, 15, 17, 19, 20, 21, and 24), which is the chamber or space defined or enclosed by the outer hose 324 and the outer lumen 328, and between the two air-tight seals 316 and 336 located at the connector section 300 and the distal section 308, respectively.

Figure 16:
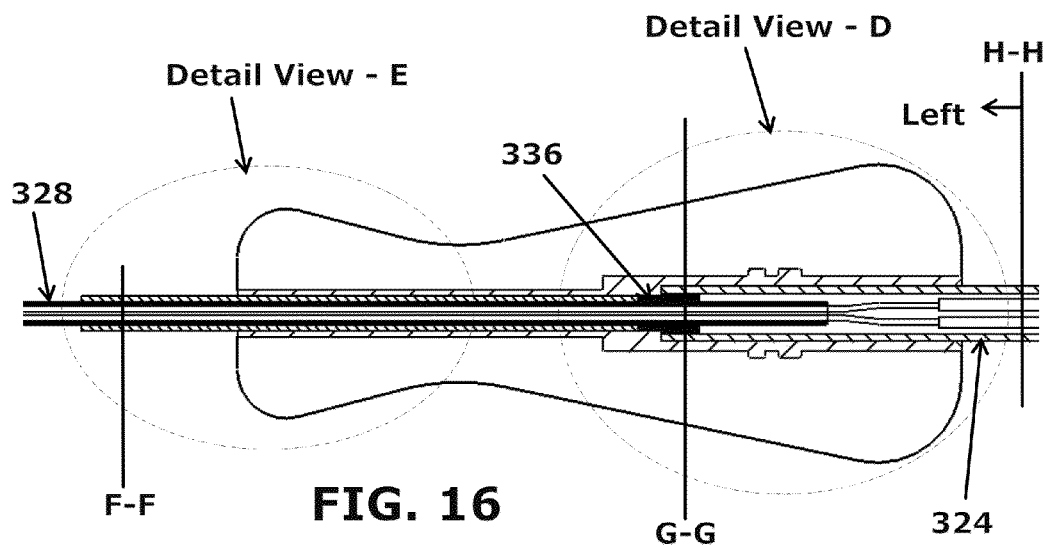
FIG. 16 is a side view of the proximal section of the catheter of FIG. 10.
Figure 17:
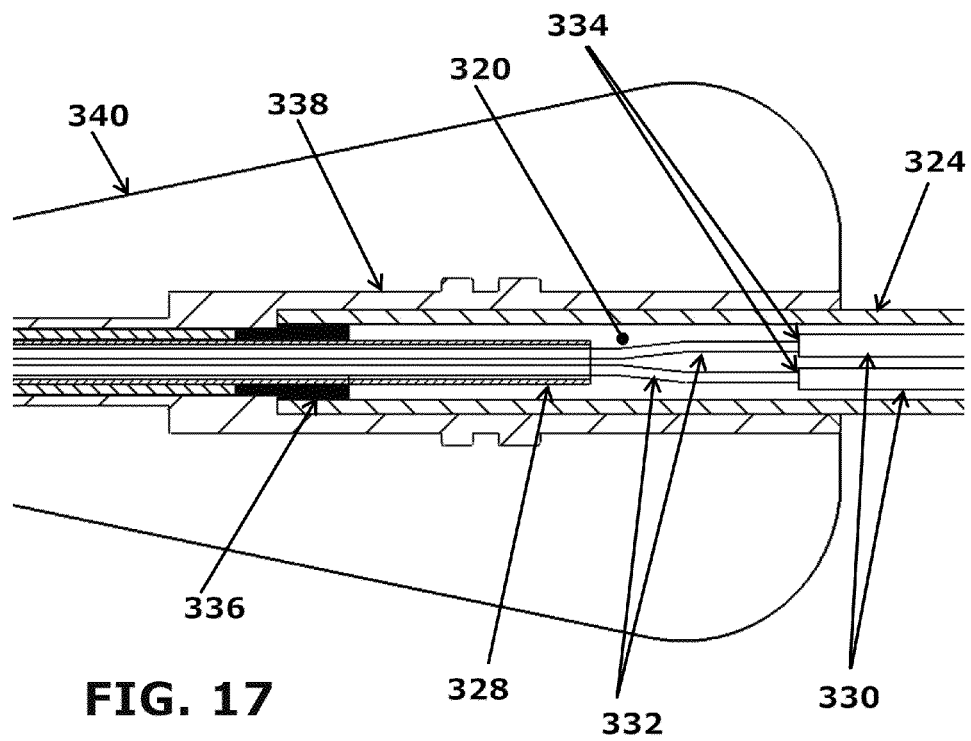
FIG. 17 is an enlarged view of the area D in FIG. 16.
Figure 20:
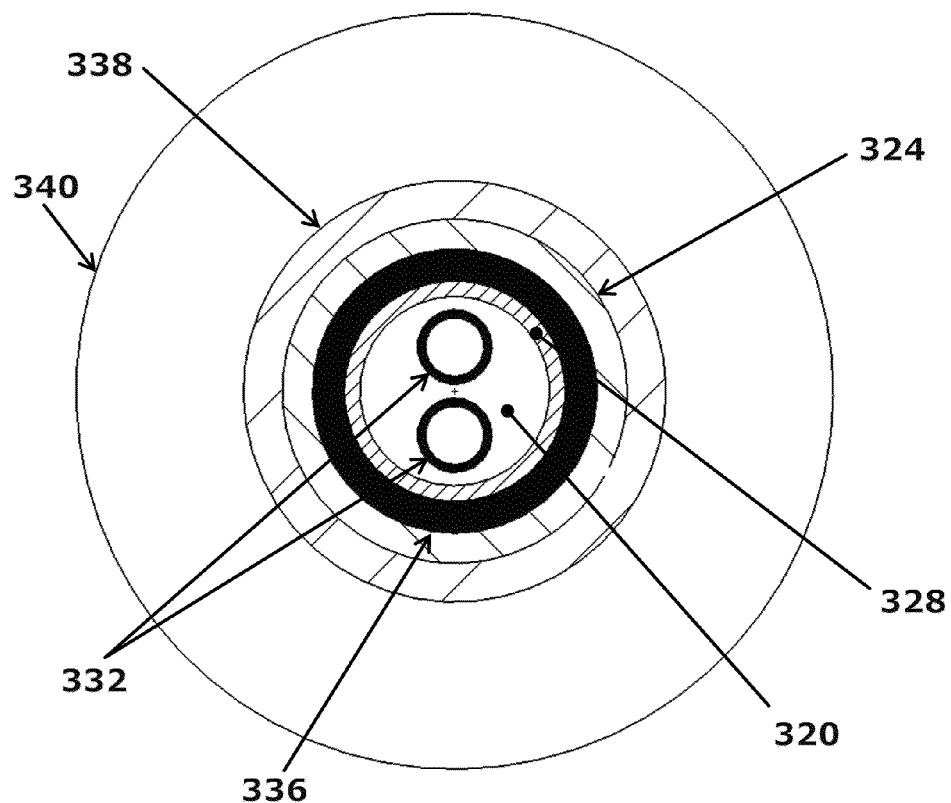
FIG. 20 is a cross-sectional view taken along line G-G in FIG. 16.
Figure 21:
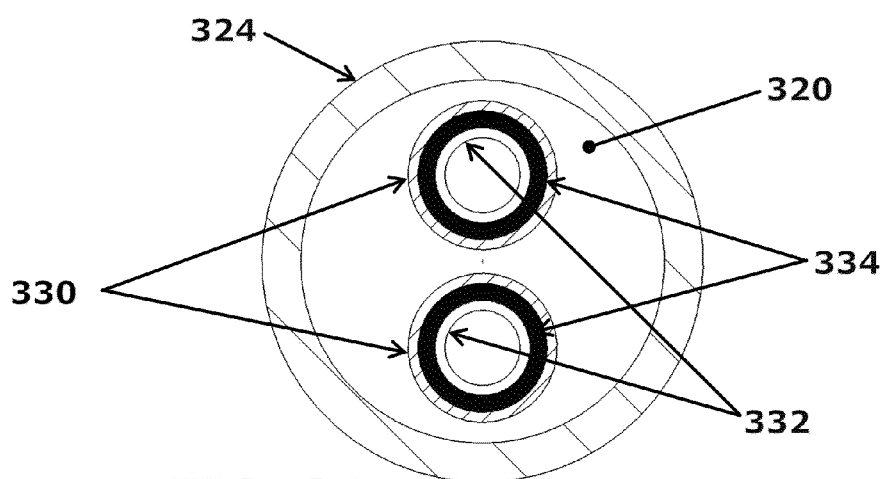
FIG. 21 is a cross-sectional view taken along line H-H in FIG. 16.
Figure 22:
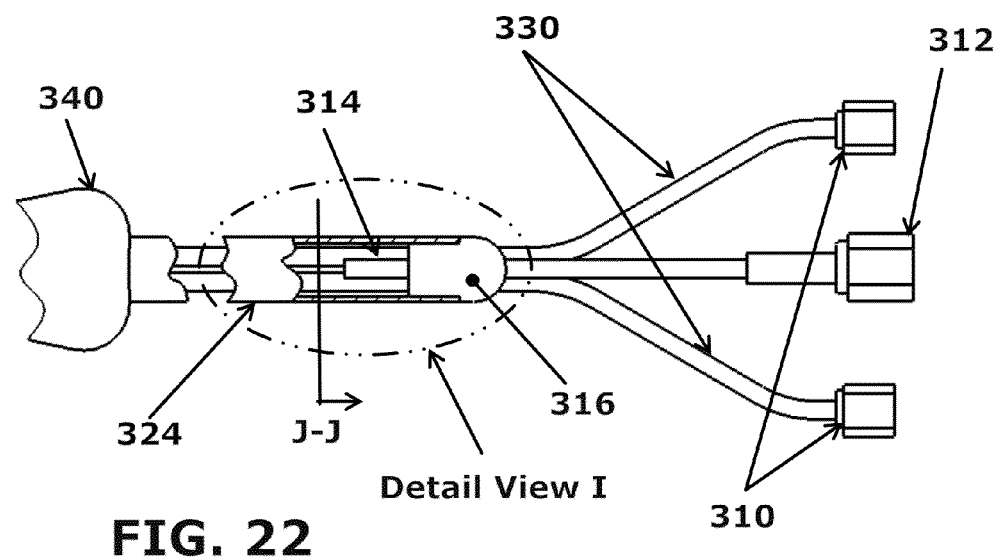
FIG. 22 is a side view of the connector section of the catheter of FIG. 10.
Figure 23:
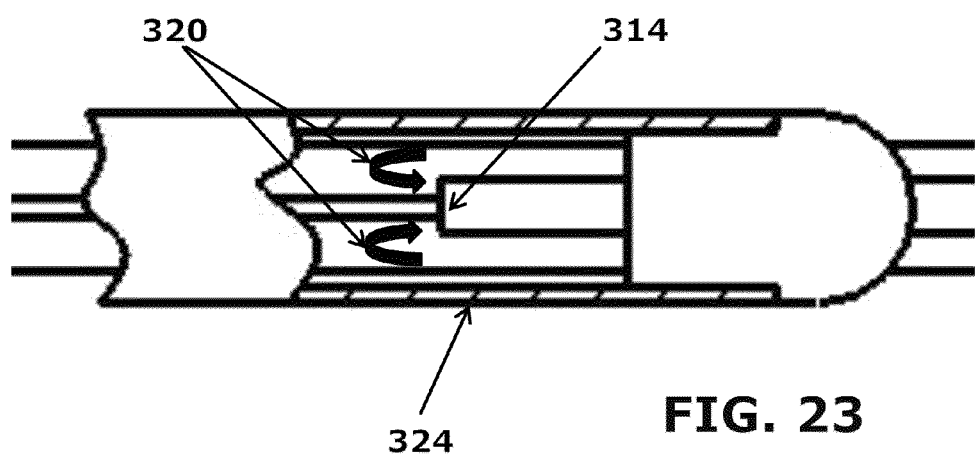
FIG. 23 is an enlarged view of the area I in FIG. 22.
Figure 24:
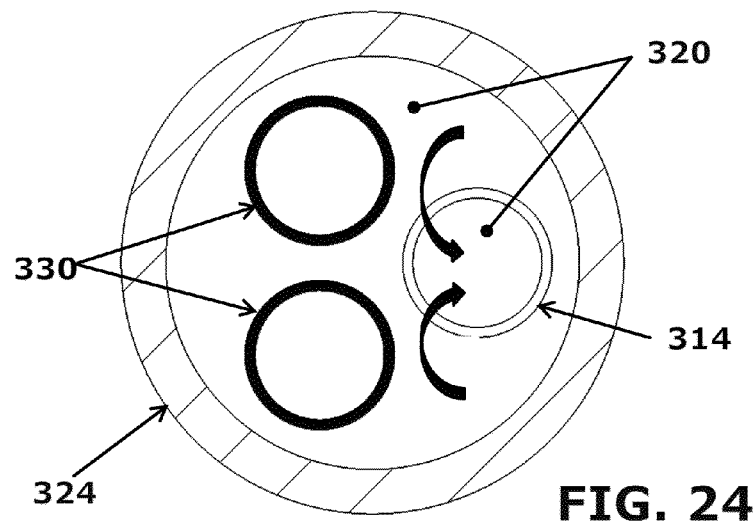
FIG. 24 is a cross-sectional view taken along line J-J in FIG. 22.

Referring to FIGS. 16, 17 and 21, the hose section 302 is structured with a flexible outer hose 324 made of nylon material. At the connector section 300, the hose 324 is sealed by epoxy to the two delivery tubes 330 and to the vacuum tube 314. At the proximal section 304, the hose 324 is sealed by epoxy to the outer lumen 328. The entire length of the hose 324 encapsulates the two delivery tubes 330 that are positioned parallel to each other inside the hose 324. The delivery tubes 330 can be made of brass alloy or copper.

Referring to FIGS. 11 and 14-19, the proximal section 304 of the catheter 102 is where the tubes transition. The larger-diameter brass alloy/copper delivery tubes 330 extending from the connector section 300 are joined with two corresponding smaller-diameter delivery tubes 332, which lead into the smaller-diameter outer lumen 328 at the other end. This is best shown in FIG. 17. The delivery tubes 332 can be made of a copper-nickel alloy. The outer lumen 328 can be a flexible tube made from Pebax material and having a reinforced stainless steel coil. The entire length of the outer lumen 328 encapsulates the two copper-nickel delivery tubes 332, which are positioned parallel to each other inside the outer lumen 328. The connections between the tubes 330, 332 are accomplished by a solder/braze material 334 (see FIG. 21). The hose 324 is also connected with the outer lumen 328 by a vacuum rated epoxy material 336 to form an airtight seal. An inner handle piece 338 and an outer handle piece 340 are assembled over the various joints to protect the joints, and to provide a user-handling interface.

A strain relief 348 (see FIGS. 18 and 19) is provided between the inner handle piece 338 and the outer lumen 328 at the distal end of the proximal section 304. The strain relief 348 is a flexible nylon tube which functions to provide strain support to the catheter body 306 by distributing absorbed energy along its length.

The catheter body 306 includes two copper-nickel delivery tubes 332 positioned parallel within an outer PEBAX™ lumen tube 328. The combination of material selections, physical sizes (as described below) and mechanical arrangement allows the catheter body 306 to be very flexible. The catheter body 306, along with the distal section 308 described below, is capable of bending around a contour having an angle of less than ninety degrees, having a bend radius of less than 0.50 inch.

The distal section 308 is a non-insulated section of the catheter 102. The present invention provides five possible embodiments for the distal section 308.

A Single-Loop Ablative Element

Referring to FIGS. 11-13, cryogen circulates from the connector section 300 to the distal section 308, and then back to the connector section 300 through a continuous pathway that forms a single-loop 350 at the distal section 308. The single pathway is defined by the tubes 330, 332, and with the single-loop 350 formed in the tube 332 that is located at the distal-most end of the distal section 308. The axis of the loop 350 is not concentric, but is perpendicular to the axis of the catheter's outer lumen 328. The delivery tube 332 is not insulated at the distal section 308 to facilitate maximum heat transfer capability.

This single-loop design is simple to manufacture and has fewer potential failure points. It minimizes the number of high-pressure connections. All the pressure joints are inside the catheter's outer lumen 328. Gas leakage within the catheter vacuum chamber 320 is captured. In addition, as described above, the system safety features monitor pressure level within the catheter vacuum chamber 320 and automatically purges unwanted gas away from the patient.

The single-loop 350 can be formed of a flexible material having good fatigue property. The material can made from annealed 70/30 Copper-Nickel alloy with an outer diameter of 0.026 inches (0.660 mm) and an inner diameter of 0.020 inches (0.508 mm). The outer diameter of the formed loop can be approximately 0.135 inches (3.429 mm), less than 11 French. The compactness as well as the flexibility of the single-loop 350 design enables it to enter the vascular structure easily.

A Twisted-Loop Ablative Element

Figure 25:
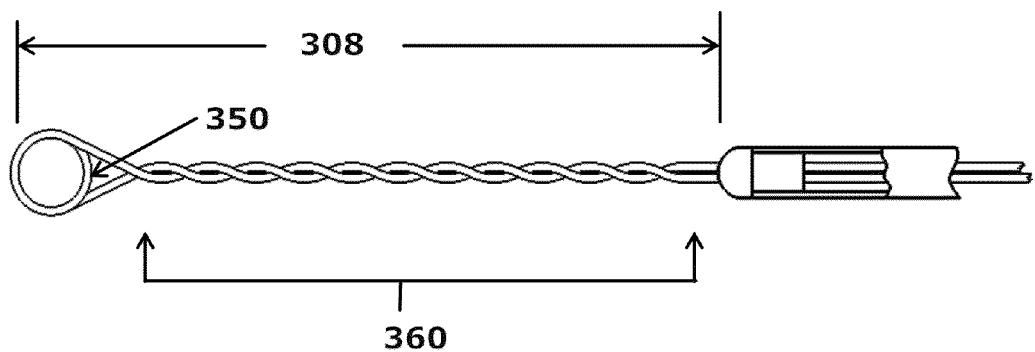
FIG. 25 is a side view of the distal section of another embodiment of the catheter of FIG. 10.

FIG. 25 illustrates a twisted-loop design for the ablative element at the distal section 308, which is a modification of the single-loop design described above. The tube 332 is twisted about itself to form a length 360 where the tube is twisted, with the twisted length 360 positioned just proximal to the single-loop 350. The twisted-loop design is functionally similar to the single-loop design described above, but with some mechanical differences. For example, the twisted-loop design has increased surface area per linear length, which results in a slight improvement in efficiency since the rate of heat conduction is proportional to its surface area. The twisted-loop is also uniformly stiffer about its circumference as opposed to the single-loop design. In general, manipulating the catheter 102 through a common passage is relatively more difficult as it requires greater applied force. However, flexing a stiffer element at a constant displacement results in higher material stress and therefore lowers its fatigue life. As an alternative, the loop 350 at the distal-most end can be replaced by a simple bend or turn.

A Bowed-Loop Ablative Element

Figure 26:
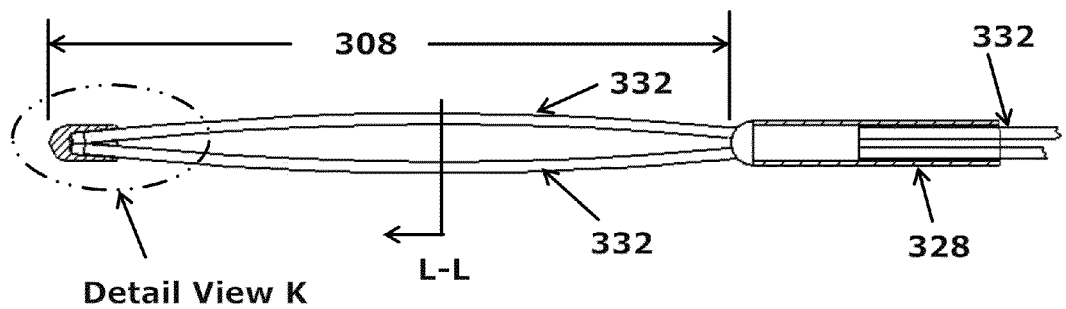
FIG. 26 is a side view of the distal section of yet another embodiment of the catheter of FIG. 10.
Figure 27:
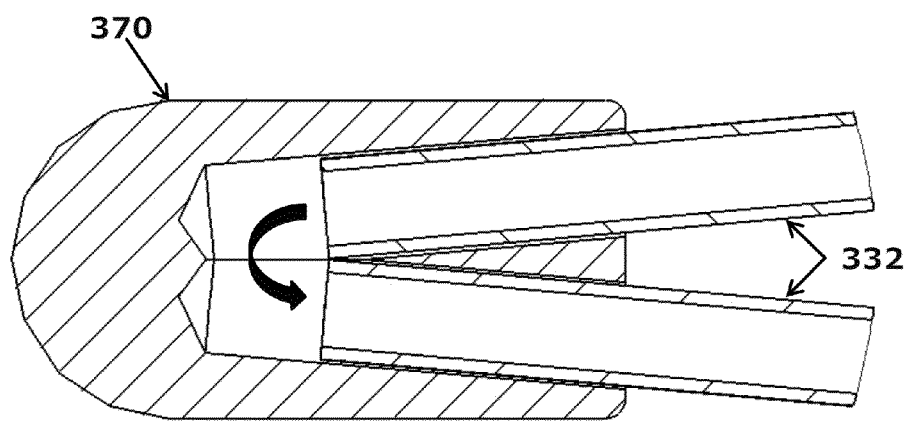
FIG. 27 is an enlarged view of the area K in FIG. 26.
Figure 28:
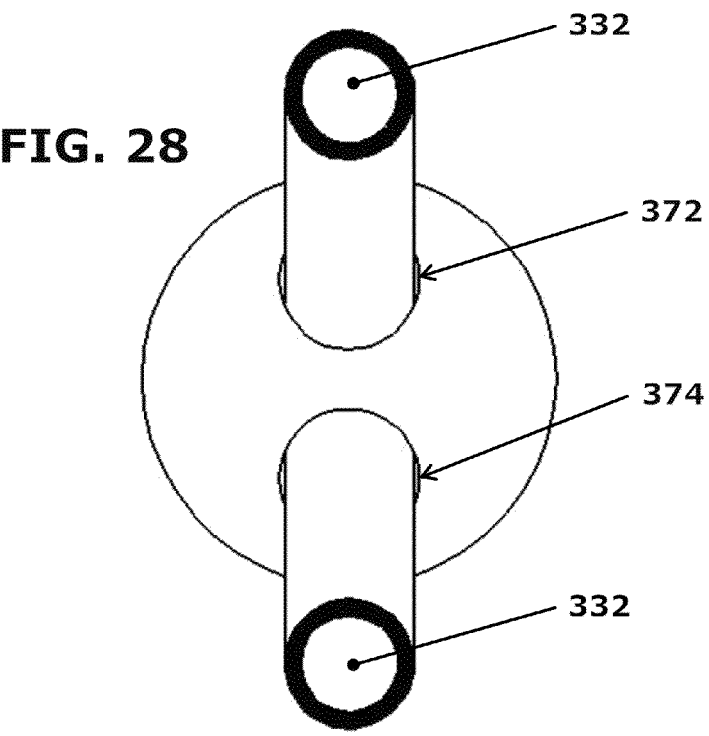
FIG. 28 is a cross-sectional view taken along line L-L in FIG. 26.

FIGS. 26-28 illustrate a bowed-loop design for the ablative element at the distal section 308. This embodiment incorporates a custom manifold 370 at the distal tip. The manifold 370 is in fluid communication with the cryogen carrying tubes 332, and has two interface holes 372 and 374 for tube connections. The interface holes 372 and 374 are positioned angularly apart, thereby creating a bowing effect on the tubes 332 when constrained at the opposite end by the outer lumen 328. The bowed configuration of the tubes 332 forces contact between the freezing elements (i.e., the tubes 332) and the ablated tissue. Energy transfers directly from the catheter to the tissue more effectively, and this embodiment is more effective when treating larger diameter vessels.

A Bowed, Multi-Return Lumens Ablative Element

Figure 29:
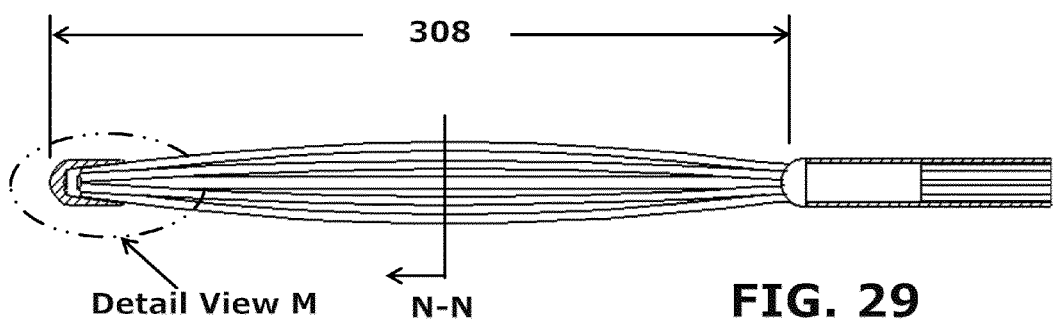
FIG. 29 is a side view of the distal section of yet a further embodiment of the catheter of FIG. 10.
Figure 30:
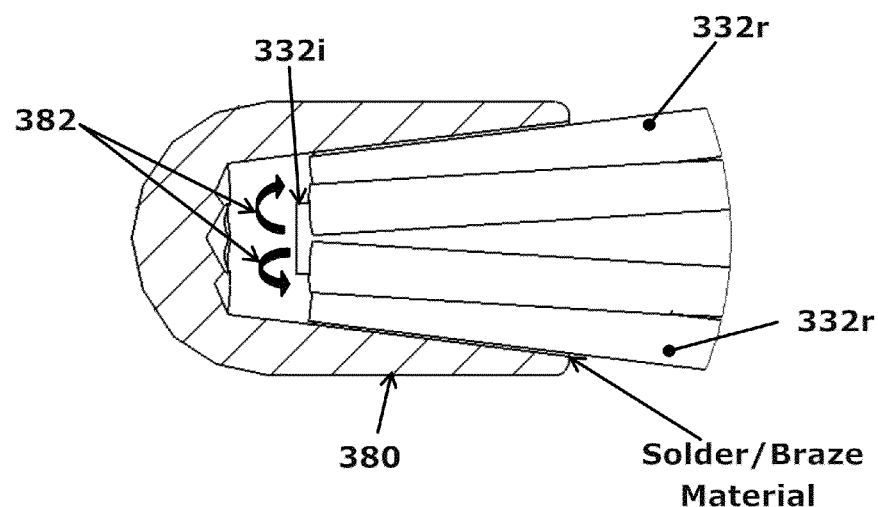
FIG. 30 is an enlarged view of the area M in FIG. 29.
Figure 31:
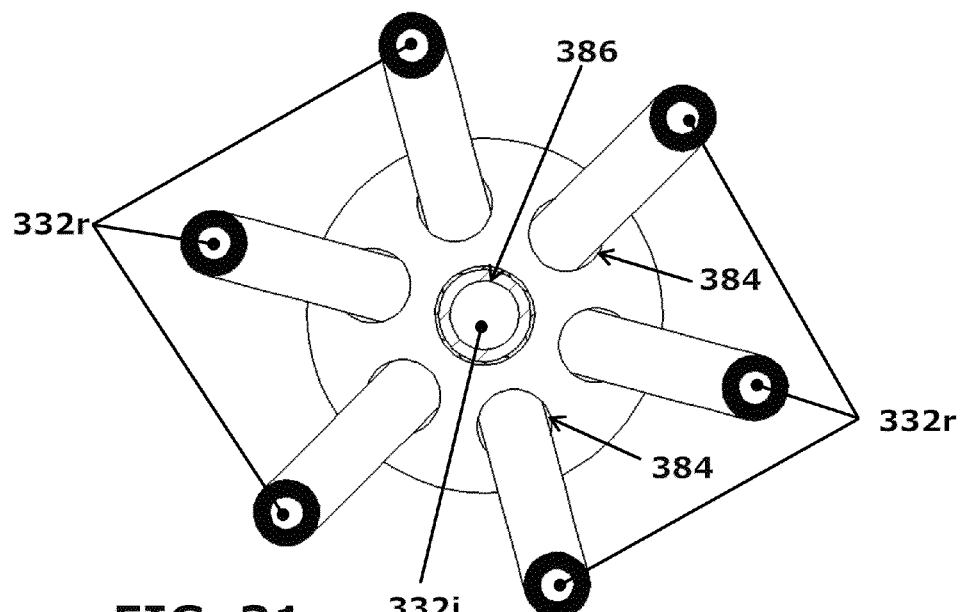
FIG. 31 is a cross-sectional view taken along line N-N in FIG. 29.

FIGS. 29-31 illustrate an embodiment having one inlet tube 332i and multiple return tubes 332r. The inlet delivery tube 332i is centered along the manifold 380 and feeds cryogen into the chamber 382 in the manifold 380. The inlet and return ports are in fluid communication within the manifold chamber 382. The manifold 380 has a circular array of mounting holes 384 for the return fluid. These holes 384 are positioned concentrically around the inlet hole 386. This design represents a modification of the bowed feature shown and described in connection with FIGS. 26-28, with a custom-machined manifold 380 having angular mounting features for the return tubes 332r. This multi-lumen design allows more effective energy distribution circumferentially around the vessel.

A Dual Single-Loop Ablative Element

Figure 32:
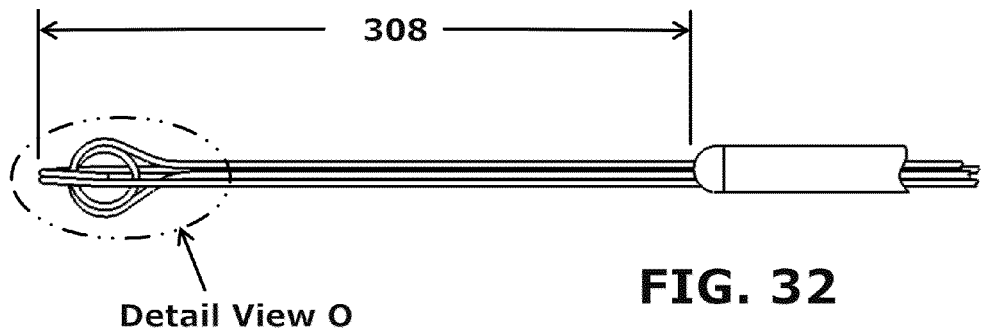
FIG. 32 is a side view of the distal section of yet a further embodiment of the catheter of FIG. 10.
Figure 33:
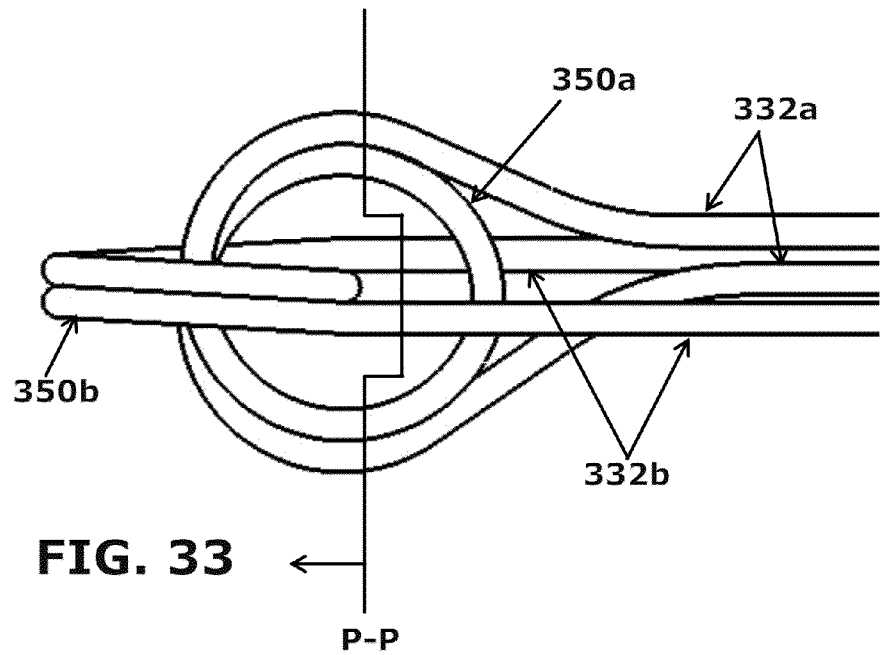
FIG. 33 is an enlarged view of the area O in FIG. 32.
Figure 34:
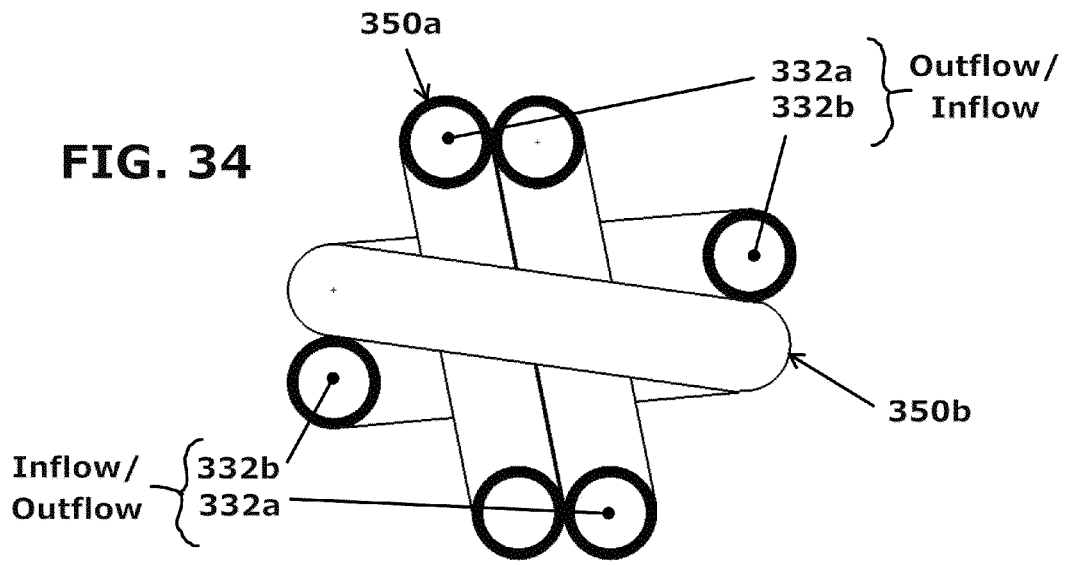
FIG. 34 is a cross-sectional view taken along line P-P in FIG. 33.

FIGS. 32-34 illustrate an embodiment having two single-loop ablative elements. This embodiment combines principles from the previous embodiments. As described in the embodiment of a single-loop ablative element, cryogen circulates from the connector section 300 to the distal section 308, and then back to the connector section 300 through a continuous pathway that forms two single-loops 350a and 350b at the distal section 308. The first single pathway is defined by the tubes 330, 332a, and with the single-loop 350a formed in the tube 332 that is located at the distal-most end of the distal section 308. The second single pathway is defined by the tubes 330, 332b, and with the single-loop 350b formed in the tube 332 that is also located at the distal-most end of the distal section 308. One of the delivery tubes 330 fluidly communicates with each of the delivery tubes 332a and 332b. The second delivery tube 330 fluidly communicates with the second set of delivery tubes 332a and 332b. The two single-loops 350a and 350b of the delivery tubes 332 join at the distal end with the loops 350a, 350b interlocked together having their loop axes perpendicular to each other. Interconnecting both loops 350a, 350b will force the ablative elements to be inseparable, resulting in focused energy delivery. This embodiment can deliver more cold energy because of the increase in flow area along the two single loops 350a, 350b. By doubling the heat transfer surface area of the ablative element along with an increase in circumferential volume taken up by the delivery tubes 332, this embodiment results in faster freeze time and larger ablative treatment region.

Figure 35:
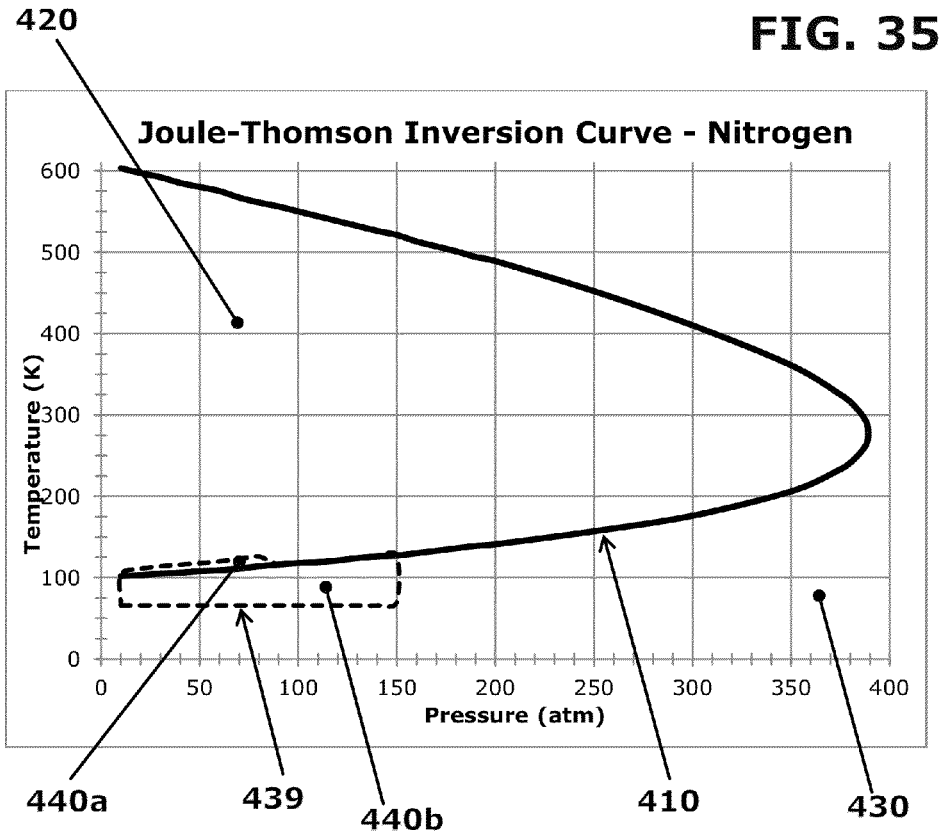
FIG. 35 illustrates an exemplary Joule-Thomson Inversion Curve for the cryogenic fluid of the present invention.

The cryogenic fluid described herein is in a liquid phase. The cryogenic fluids of the present invention are designed to have its inlet operating temperature and pressure on its Joule-Thomson (J-T) Inversion Curve. FIG. 35 illustrates a J-T Inversion Curve 410 for the nitrogen gas of the present invention. The curve was generated from data provided by the National Institute of Standards and Technology (NIST) Chemistry WebBook. When a real fluid expands at a constant enthalpy or a J-T expansion, fluid temperature can increase, decrease, or remain constant depending on the initial temperature and pressure. A J-T Inversion Curve 410 separates the region where the fluid heats up 430 and cools down 420 during an expansion process. The J-T Inversion Curve is defined by two parameters, pressure, and temperature. The J-T Coefficient within the heating region 430 has a negative value and a positive value within the cooling region 420. Along the J-T Inversion Curve, the J-T Coefficient is zero. The J-T Coefficient is defined by the ratio of temperature change over pressure change at constant enthalpy. The cryogenic fluid of the present invention operates at a point on its J-T Inversion Curve wherein the J-T Coefficient can vary within 0.00±0.08 degrees F./atmosphere. The dashed lines 439 shown on FIG. 35 define the region 440 where the J-T Coefficient is within 0.00±0.08 degrees F./atmosphere. Region 440a defines the positive J-T Coefficient having values within the range of 0.00 to 0.08 degrees F./atmosphere. Region 440b defines the negative J-T Coefficient having values within the range of −0.08 to 0 degrees F./atmosphere.

The intention is to preserve the quality of the sub-cooled fluid transported to the catheter 102. This can be achieved by eliminating the effect of pressure changes due to fluid expansion/contraction along non-uniform flow passages leading to the catheter distal section 308 from the ablation system 106, in addition to other factors such as insulation. In the region away from the J-T Inversion Curve, pressure change results in temperature changes that alter the quality of the original fluid. By operating along the J-T Inversion Curve, constant fluid temperature can be supplied to the targeted area. The outcomes are controllable energy supply and predictable treatment level. Once the cryogenic fluid enters the catheter distal section 308, it absorbs heat from the surrounding, resulting in changes in fluid temperature, pressure, and phase. The degree to which these parameters change depends mostly on the thermal property of the surrounding tissue, the catheter construction and material, and cryogen flow rate, among others. The fluid exiting the catheter distal section 308 departs from the original operating point on the J-T Inversion Curve. It is not critical for the catheter return gas to operate on the J-T Inversion Curve. The function of the return gas is only for pre-cooling purposes.

The cryogenic fluid utilized is preferably liquid nitrogen. However, other cryogenic fluids may be utilized such as argon, neon, or helium. Liquid nitrogen contains very potent cold energy along with other properties making it an ideal fluid for cryoablation. It has high thermal capacity and fluid density, which means that it carries more cold energy in smaller volumes. As a result, liquid nitrogen can absorb a higher amount of heat energy for every degree change in its temperature as opposed to operating in other phases of nitrogen. With liquid nitrogen being a dense fluid, mass flow rate delivering to catheter distal end is possible through smaller tubing at a constant pressure. This allows for a more compact design. In addition to its specific heat energy (thermal capacity), liquid nitrogen also carries enthalpy heat energy. Enthalpy of vaporization or heat of evaporation of liquid nitrogen can further absorb heat while remaining at a constant temperature. Furthermore, liquid nitrogen has good thermal conductivity allowing absorbed heat to spread and dissipate efficiently.

While the description above refers to particular embodiments of the present invention, it will be understood that many modifications may be made without departing from the spirit thereof. The accompanying claims are intended to cover such modifications as would fall within the true scope and spirit of the present invention.

The invention claimed is:

1. A cryoablation system, comprising:
 a gas source which provides a working nitrogen gas at room temperature and at a constant set pressure;
 a liquid generator which is coupled to the gas source to receive the working gas, the liquid generator configured to generate a working cryogen fluid in a liquid phase that operates at a temperature and pressure that lies on its Joule-Thomson Inversion Curve, with a Joule-Thomson coefficient maintained within the range $0.00\pm0.08$ degrees F./Atmosphere; and
 a catheter coupled to the liquid generator for receiving the working cryogen, the catheter having a distal section which delivers the working cryogen to a treatment location.

2. The system of claim 1, wherein the liquid generator includes a storage tank that contains a cryogenic refrigerant for cooling the working gas.

3. The system of claim 2, wherein vaporized cryogen gas from the storage tank is used to cool the incoming working gas.

4. The system of claim 2, wherein the working gas is also cooled by the working cryogen that is returned from the catheter.

5. The system of claim 1, further including a vacuum pump for providing thermal/vacuum insulation.

6. The system of claim 5, wherein the vacuum pump evacuates unwanted gas leakage from the catheter.

7. The system of claim 1, further including a leakage monitoring and detection system that includes an automated purge and shutdown procedure.

8. The system of claim 1, further including a thaw module that thaws the catheter, the thaw module operating to thaw the catheter by using either room temperature, or room temperature combined with a heater.

* * * * *